(12) United States Patent
Daners

(10) Patent No.: US 6,275,786 B1
(45) Date of Patent: *Aug. 14, 2001

(54) DEVICE FOR MONITORING A NEUTRAL ELECTRODE DURING HF SURGERY

(75) Inventor: Felix Daners, Schaffhausen (CH)

(73) Assignee: Storz Endoskop GmbH (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,242

(22) PCT Filed: Apr. 14, 1998

(86) PCT No.: PCT/EP98/02153

§ 371 Date: Dec. 22, 1999

§ 102(e) Date: Dec. 22, 1999

(87) PCT Pub. No.: WO98/44855

PCT Pub. Date: Oct. 15, 1998

(30) Foreign Application Priority Data

Apr. 10, 1997 (DE) ................................................ 197 14 972

(51) Int. Cl.[7] .............................. G06F 9/44; G06F 13/10; G06F 13/12; G06F 17/50
(52) U.S. Cl. ............................................... 703/18; 703/20
(58) Field of Search ........................................ 703/20, 18

(56) References Cited

U.S. PATENT DOCUMENTS

| | | |
|---|---|---|
| 4,651,280 | 3/1987 | Chang et al. . |
| 4,741,334 | 5/1988 | Irnich . |
| 4,754,757 | 7/1988 | Feucht . |
| 5,406,503 | 4/1995 | Williams, Jr. et al. . |
| 5,720,744 * | 2/1998 | Eggleston et al. .................... 606/40 |

FOREIGN PATENT DOCUMENTS

| | | |
|---|---|---|
| 32 39 640 C2 | 1/1987 | (DE) . |
| 0 390 937 A1 | 10/1990 | (EP) . |

OTHER PUBLICATIONS

Jankauskas et al.; ECG sampling unit for electrosurgical environments; IEEE 1988 Bioengineering Conf.; pp. 79–81.*

* cited by examiner

Primary Examiner—Kevin J. Teska
Assistant Examiner—Hugh Jones
(74) Attorney, Agent, or Firm—St. Onge Steward Johnston & Reens LLC

(57) ABSTRACT

The invention refers to a device for monitoring the application of a neutral electrode in unipolar HF surgery, having an impedance sensor with a resonant circuit comprising a secondary coil of a transformer and HF input capacitors of preferably two partial electrode surfaces. The impedance sensor detects the transient impedances of two partial electrode surfaces connected in series with the patient's tissues by application of a patient auxiliary current and is moderated by the transition impedances.

The invention is characterized in that the resonant circuit is excited by alternating voltages of variable frequencies in the range of a resonant frequency, and in that a peak value detector is provided which detects an alternating voltage peak value at the resonant frequency.

The disclosed device excites the resonant circuit in such a manner that a faultless measurement of the transition impedance at the level of the patient's tissues is made possible.

16 Claims, 2 Drawing Sheets

DEVICE FOR MONITORING A NEUTRAL ELECTRODE DURING HF SURGERY

FIELD OF THE INVENTION

This invention relates to a device for monitoring the application of a two-art neutral electrode during unipolar high-frequency surgery.

BACKGROUND OF THE INVENTION

During high-frequency surgery, if the actual area of contact between the neutral electrode and the patients body is too small there is a risk of receiving burns from the neutral electrode due to the large current densities which then occur.

Devices for monitoring the application of neutral electrodes in high-frequency surgery are known from DE 32 39 640 C2 or EP 0 390 937 A1. The DE 32 39 640 C2 reference discloses such a device having an impedance sensor with a resonant circuit comprising a secondary coil of a transformer and HF input capacitors of preferably two partial electrode surfaces. The impedance sensor detects the transition impedances of two partial electrode surfaces connected in series with the patient's tissues by application of a patient auxiliary current, and is moderated by the transition impedances. If this resonance network is excited at its exact resonant frequency, the patient transition resistance R alone becomes visible. This operating point can be attained in principle by positive voltage feedback. However, it has been found that such arrangements are vulnerable to interference signals produced by HF generators. As such, a positive voltage feedback would have to be tapped behind a filter, the phase shift of which depends on the tolerances of the components used to construct the filter. This phase shift has a large impact on the resulting closed loop oscillation frequency of the system. The parallel resonant circuit is then no longer excited at its exact resonant frequency, which results in measurement errors. Furthermore, such a system is typically not very accurate due to the tolerances of the relatively large number of components involved.

SUMMARY OF THE INVENTION

It is therefore an object of the invention to provide a device for unipolar HF surgery which excites the resonant circuit in such a manner that a more precise measurement of the transition impedance of the patient's tissues is made possible.

This and other objects of the invention are achieved by provision of a resonant circuit which is excited by alternating voltages of variable frequencies in the range of a resonant frequency, and a peak value detector which detects an alternating voltage peak value at the resonant frequency.

Contrary to conventional measuring devices, which are affected by phase errors caused by component tolerances, the device according to the invention dispenses with any use of feedback signals, which could be altered by large interference signals. Instead, the peak value detector determines the alternating voltage peak value at the resonant frequency. While the frequency of the exciting voltage continuously varies, generally being repeatedly passed over in a frequency sweep, the peak value detector, which has a time constant substantially greater than the duration of a single frequency variation or of a single sweep, stores the detected peak value. This corresponds to the patient transition resistance at the resonant frequency, which itself is not determined at all in accordance with the invention, but which is the voltage which would be measured when the resonance circuit is excited at the exact resonance frequency. Measuring errors of conventional devices which attempt to match the exact resonant frequency are avoided by the selection of the peak value detected during the frequency variation as the patient transition resistance.

To permit self-testing of the impedance sensor's function, i.e., without a HF generator, a further development of the invention provides for a reference resonant circuit that can be connected instead of the normal resonant circuit via a switch. It is advantageous for the reference resistance at the resonant frequency to be greater than the highest patient transition resistance at which activation of the HF generator power is still permitted. This ensures that no HF use is possible if the switch fails on being switched back to the resonance network.

The systems or devices for monitoring the application of neutral electrodes known from the cited prior art produce a signal if the adherence of the neutral electrode has become so poor that the HF generator may no longer be activated. With the HF generator switched on, the HF output is suddenly shut off due to the excessively high transition resistance of the neutral electrode. Conventional devices are therefore unsuitable for calling the surgeon's attention to a deterioration of the adherence of the neutral electrode or for supplying information regarding the quality of the application while the neutral electrode is being applied. It is therefore desirable to provide continuous monitoring of the application of the neutral electrode and determination of the quality of the application even while the neutral electrode is being applied.

In this regard, the invention is preferably capable of determining how well the neutral electrode is functioning even during its application. With this being the case, during the surgical operation, it is possible to determine if the current density is rising and will soon reach a critical value at which the generator can no longer be activated. Moreover, this also makes it possible to determine whether the neutral electrode is suitable for the planned surgery on the basis of its physical properties, its expansion and its placement, or if the neutral electrode is inadequate for the planned surgery.

In a system for unipolar HF surgery with a simple, divided neutral electrode, the difference of the currents flowing through the two parts of the neutral electrode, aside from the transition resistance, can typically be analyzed in a manner that is known per se as a parameter for describing the quality of the application. Thus, in addition to the impedance sensor, which detects the series-connected transition resistances of the two partial electrode surfaces by application of a patient auxiliary current, it may be desirable to provide a current asymmetry sensor as well.

The current asymmetry sensor detects the difference between the HF currents flowing through the two partial electrode surfaces when the HF output signal is activated, and the rectified value of the patient auxiliary current between the two partial electrode surfaces when the HF output signal is deactivated. The output signals of the impedance sensor and of the current asymmetry sensor are supplied to an electronic control and analysis means which derives a signal for monitoring the sensor function from the signals of the impedance sensor and of the current asymmetry sensor. A control and analysis unit can also use the momentary value of the current asymmetry in relation to a HF current, as well as the first derivation of this relative current asymmetry in time, as criteria for this in addition to the momentary transition resistance.

Furthermore, for practical purposes the electronic control and analysis means sets the output signals of the impedance sensor and of the current asymmetry sensor in relation to the selected generator setting. In such case, a fuzzy-logic function linking the individual parameters together can be used for the analysis and linking processes in addition to fixed criteria for the transition impedance and the asymmetry.

Finally, the invention can have an optical and/or acoustic indicator such as a bar indicator, which displays the quality of the application of the neutral electrode and warns the surgeon of an impending failure of the neutral electrode.

BRIEF DESCRIPTION OF THE DRAWINGS

The invention and its particular features and advantages will become more apparent from the following detailed description considered with reference to the accompanying drawings, in which.

DETAILED DESCRIPTION OF THE INVENTION

Large interference signals with the HF generator activated are problematic in the implementation of monitoring the impedance of a neutral electrode (NE). In order for the HF current to be supplied symmetrically to the partial electrode surfaces, each partial surface of the neutral electrode is ordinarily connected via a capacitor (2*CC) to the same pole (HFRET) of the HF generator, as shown in FIG. 2.

Figure 2:
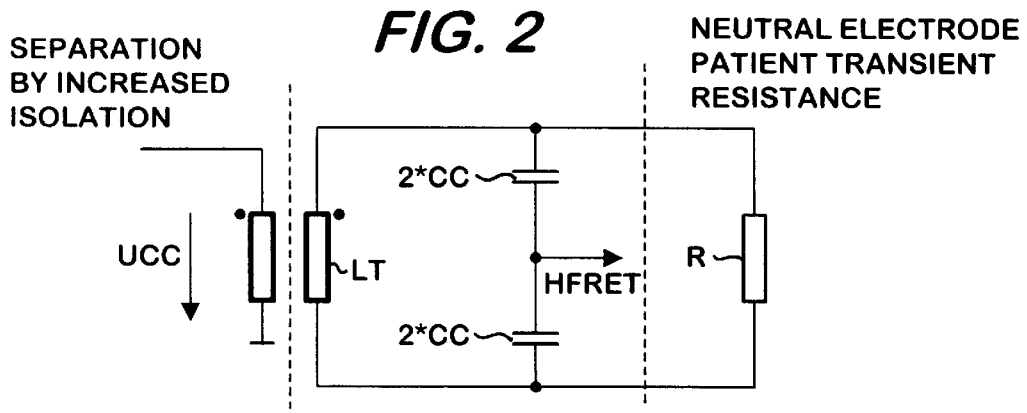
FIG. 2 illustrates the structure of a resonance network and of a HF coupling which may be employed by a device for monitoring a neutral electrode during HF surgery in accordance with the present invention.

Also as shown in FIG. 2, the device for detecting the patient transition impedance and/or transition resistance is electrically isolated from the partial electrode surfaces. A transformer with its secondary coil (LT) connected between the partial electrode surfaces is used for this isolation. The primary side of the transformer lies on the potential of an electronic control and analysis means.

The secondary coil (LT) of the transformer for the resistance transformation forms a parallel resonance together with the input capacitors (2*CC), which resonance is moderated by the patient transition resistance (R).

Figure 1:
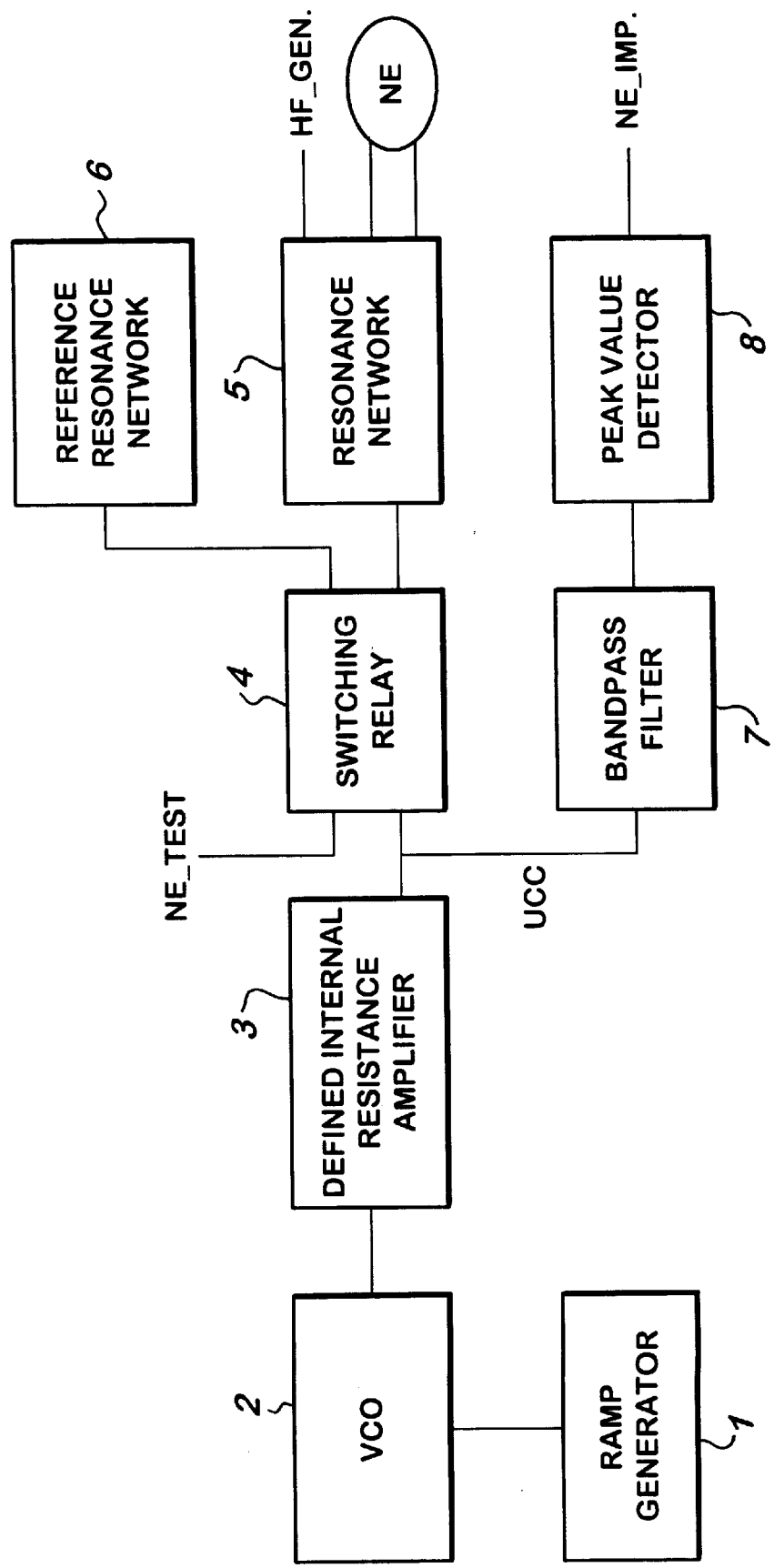
FIG. 1 illustrates the structural principle of an impedance sensor which may be employed by a device for monitoring a neutral electrode during HF surgery in accordance with the present invention.

The resonance network, i.e., the parallel resonance from the transformer magnetizing reactance secondary coil (LT) and the input capacitors (2*CC), is excited by a frequency sweep, i.e. by varying frequencies. A voltage controlled oscillator (2), or VCO, controlled by a ramp generator (1) is used for this purpose, as shown in FIG. 1, and its output signal is supplied to an amplifier (3) with a defined inner resistance.

The VCO (2) sweeps the entire parallel resonant frequency range in order for the resonant frequency to be found. The VCO (2) preferably comprises a circuit that does not require a frequency adjustment.

The ramp generator (1) includes two comparators to permit the minimum and maximum voltages of the voltage ramp to be precisely set. In addition, the ramp generator (1) typically has a rise and fall time of approximately 6 ms. The rise time also corresponds to the scanning rate at which the patient transition resistance between the partial electrode surfaces is measured.

The output signal of the amplifier (3) is applied via a switching relay (4) either to the resonance network (5) shown in FIG. 2, or to a reference resonance network (6) to be explained further below.

When a voltage is applied to the resonance network (5) or the reference resonance network (6), the input impedance of the respective network is always greatest at the exact resonant frequency, and corresponds to the patient transition resistance (R) between the partial electrode surfaces. Since each respective resonance network is excited by a voltage source with a defined inner resistance, namely by the amplifier (3), the greatest voltage amplitude is always applied to the parallel resonance network precisely at the resonant frequency.

Figure 3:
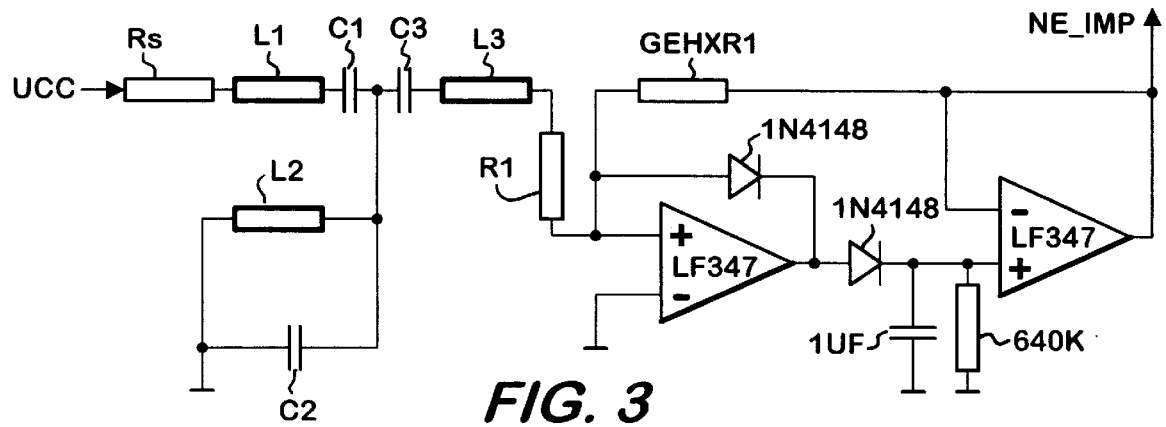
FIG. 3 illustrates the structure of a band pass filter, a peak value detector, and a measurement signal amplifier which may be employed by a device for monitoring a neutral electrode during HF surgery in accordance with the present invention.

A band pass filter (7) and a peak value detector and measurement signal amplifier (8) are used to determine the resonant frequency. Details of their structure are represented in FIG. 3.

The band pass filter (7) has a wide pass band and offers good damping properties against interference signals. For example, the bandwidth of the pass band takes into account initial tolerances of components used, shifts due to changes in temperature or aging processes, and a safety margin, so that the resonant frequency is detected more accurately. Since it is the greatest voltage amplitude that is evaluated, the magnitude of the frequency response of the filter is what counts, and no demands are made to examine the phase angles of the filter frequency response.

The HF voltage (UCC) produced by the amplifier (3), which is also applied to the parallel resonance network (shown in FIG. 2), is supplied via the band pass filter (7) to a peak value detector (8), by which it is measured. The time constant of the detector is far greater than the time required for a frequency sweep. In this way a voltage (NE—IMP) is applied at the detector output terminal which depends substantially only on the patient transition resistance (R) between the partial electrode surfaces, on the inner resistance of the exciting voltage source (3), and on the voltage of the exciting voltage source (3). The voltage (NE_IMP) can then be analyzed by a suitable electronic analyzer not shown here.

The reference resonance network (6) is provided for self-testing of the functioning of the impedance sensor, i.e. without a HF generator. It can be connected instead of the resonance network (5) to the electronic sensor means by a switching relay (4). The reference resonance network is made up of a parallel resonant circuit comprising a small fixed inductance, a capacitance, and a reference resistance. The inductance and the capacitance roughly correspond to the values of the resonance network. The reference resistance is larger than the highest patient transition resistance that still permits an activation of the HF generator power. This ensures that no activation is possible if the switching relay (4) fails upon being switched back to the resonance network.

Thus, the sensor output voltage (NE_IMP) must lie within a precisely preset voltage window when the impedance sensor is switched to the resonance network. In the event of faulty performance the patient auxiliary current can be switched off with the same switching relay. An input signal (NE_TEST) is provided which controls the switching relay (4) and, more specifically, which switches between self-testing and monitoring of the patient transition resistance with the HF generator deactivated.

The working frequency bandwidth must be selected at a magnitude sufficient to reliably capture the resonant frequency even in view of initial tolerances of the components used, or shifts caused by the influence of temperature or aging processes. It has been found that a working frequency band ranging from 40–80 kHz is suitable. This working frequency is sufficiently far enough from the working frequency of the HF generator to provide acceptable results, and this working frequency permits a relatively large patient auxiliary current, which facilitates the measurement of small transition resistances between the partial electrode surfaces.

Sufficiently large input capacitors must be employed to prevent the interference voltages at the impedance sensor from becoming too large with the HF generator activated.

A Butterworth configuration of the $6^{th}$ order is used as the band pass in the filter shown in FIG. 3. It has a damping of approximately 38 dB with respect to the fundamental oscillation of the HF generator.

The filter is represented by a T element with a series resonance (L1), (C1), (Rs) at the input terminal, a parallel resonance (C2), (L2) in the middle, and a second series resonance (L3), (C3), (R1) at the output terminal. The filter output voltage is fed to the peak value detector, which simultaneously amplifies by the gain factor.

The settling time of the filter should be taken into account for the dimensioning of the ramp generator. It is smaller than the settling time of the resonance network by a factor of approximately 5.

Figure 4:
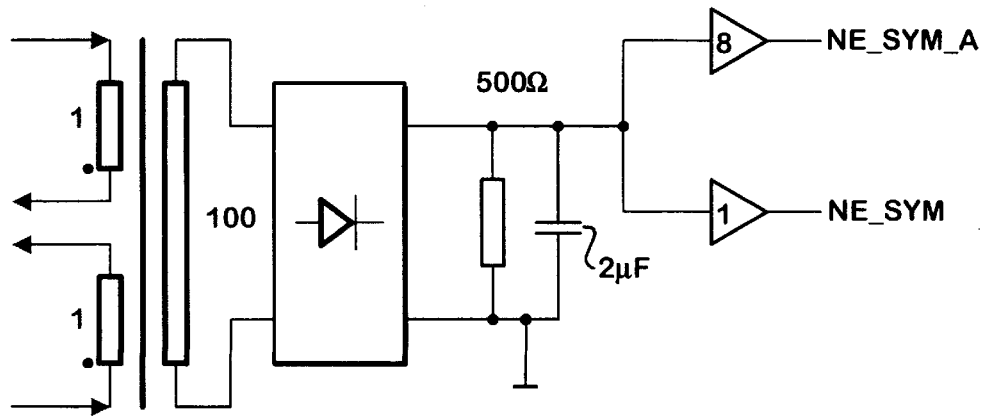
FIG. 4 illustrates the structure of a current asymmetry sensor which may be employed by a device for monitoring a neutral electrode during HF surgery in accordance with the present invention.

FIG. 4 shows the current asymmetry sensor. The current asymmetry in the two partial electrode surfaces is most easily measured with the aid of a compensating transformer with a measuring winding of 100. The leads of the partial neutral electrode surfaces are inserted in crossed relationship through the central bore of the transformer. In this way the currents flowing in the same direction cancel each other. The resulting current signal on the measuring winding corresponds exactly to the transformed asymmetrical current in the partial electrode surfaces.

For the signal to stay independent of the polarity of the generator voltage, it is rectified by a bridge rectifier. The terminating resistance is disposed behind the bridge rectifier.

The maximum current value to be measured is 1.6 A. This fixes the terminating resistance at 500Ω, so that the sensor voltage amounts to 8 V at maximum current. The voltage at this terminating resistance is smoothed with a capacitor. Thus, the voltage at the capacitor represents the rectified value of the differential current.

To permit the small auxiliary current in patients tissues to be analyzed in standby mode, the voltage is amplified by an additional amplifier via the capacitor by a factor of 8. The output signals (NE_SYM_A) and/or (NE_SYM) are supplied in turn to the analyzer unit not shown.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A device for monitoring the application of a unipolar neutral electrode with two separated neutral electrode partial surfaces during unipolar HF surgery, whereby the two separated neutral electrode partial surfaces are respectively connected via a HF input capacitor to source terminal, said device comprising:

an impedance sensor comprising an excitation source that excites a resonant circuit by variable frequencies in a range which includes a resonant frequency, the resonant circuit being provided by the HF capacitors to source terminal and a secondary coil of a transformer, the secondary coil being connected between the two separated neutral electrode partial surfaces and serving as excitation input, and the resonant circuit being attenuated by transition impedances of the two separated neutral electrode partial surfaces connected in series to a patients tissues;

a peak value detector which detects an alternating voltage peak value at the resonant frequency via the secondary coil of the transformer;

a voltage controlled oscillator for providing the excitation source, said voltage controlled oscillator being controlled by a ramp generator;

a current asymmetry sensor comprising a compensating transformer, said current asymmetry sensor detecting a mean value of a periodic quantity of a difference in currents flowing through the two separated neutral electrode partial surfaces during the deactivation of a HF output signal; and an electronic control and analysis means, said electronic control and analysis means deriving a signal for the quality of the application of the unipolar neutral electrode from signals of the impedance sensor and of the current asymmetry sensor.

2. The device according to claim 1, characterized in that said resonant circuit is excited by a current source with a defined inner resistance.

3. The device according to claim 1, characterized by a band pass filter detecting the alternating voltages and taking into account initial tolerances of components used and shifts due to temperature or aging processes.

4. The device according to claim 2, characterized by a reference resonance network connected to the voltage source during a deactivation of a HF output signal, for self-testing purposes.

5. The device according to claim 4, characterized in that said reference resonance network has an impedance at the resonant frequency which is greater than the maximum value of the transient impedance.

6. The device according to claim 1, characterized by an electronic control and analysis means for analyzing the characteristic of the transition impedance.

7. The device according to claim 6, characterized in that said electronic control and analysis means switches off a HF voltage if a maximum transition impedance value is exceeded.

8. The device according to claim 7, characterized in that said electronic control and analysis means indicates whether the density of a current flowing through the patients tissues is rising and approaching a critical value at which the HF voltage is switched off.

9. The device according to claim 1, characterized in that a secondary coil of said compensating transformer is connected to a primary coil of said current asymmetry sensor.

10. The device according to claim 1, characterized in that said resonant circuit comprises two partial electrode surfaces, and also in that feed lines of said partial electrode surfaces are guided in opposite directions through a central bore of said compensating transformer so that the current asymmetry is directly measurable.

11. The device according to claim 7, characterized in that said electronic control and analysis means evaluates the ratio of the current asymmetry to a HF current, and the change of this ratio in time.

12. The device according to claim 11, characterized by a current asymmetry sensor, and in that said electronic control and analysis means rectifies and amplifies the signal of said current asymmetry sensor.

13. The device according to claim 5, characterized in that said electronic control and analysis means has a fuzzy-logic function for linking the signals of said impedance sensor and those of said current asymmetry sensor to parameters of said device for HF surgery.

14. The device according to claim 7, characterized in that said electronic control and analysis means has an indicator which indicates how high the current density is and whether it is rising and will soon reach a critical value at which said HF voltage generator can no longer be activated.

15. The device according to claim 1, characterized in that said resonant circuit comprises a secondary coil of a transformer and HF input capacitors.

16. The device according to claim 1, characterized in that said resonant circuit comprises two partial electrode surfaces connected in series to a patient's tissues.

* * * * *